(12) United States Patent
Saettone et al.

(10) Patent No.: US 6,346,273 B1
(45) Date of Patent: Feb. 12, 2002

(54) PROCESS FOR SOLUBILIZING PHARMACEUTICALLY ACTIVE INGREDIENTS IN WATER AND IN AQUEOUS VEHICLES

(75) Inventors: Marco Fabrizio Saettone; Boris Giannaccini, both of Viareggio (LU); Enrico Boldrini; Pietro Bianchini, both of Pisa, all of (IT)

(73) Assignees: Farmigea S.p.A.; Marco Fabrizio Saettone; Boris Giannaccini, all of (IT)

( * ) Notice: Subject to any disclaimer, the term of this patent is extended or adjusted under 35 U.S.C. 154(b) by 0 days.

(21) Appl. No.: 09/463,331

(22) PCT Filed: Jul. 22, 1998

(86) PCT No.: PCT/IT98/00206

§ 371 Date: Jan. 21, 2000

§ 102(e) Date: Jan. 21, 2000

(87) PCT Pub. No.: WO99/04823

PCT Pub. Date: Feb. 4, 1999

(30) Foreign Application Priority Data

Jul. 23, 1997 (IT) .......................................... RM97A0456

(51) Int. Cl.[7] ................................................ A61K 9/14
(52) U.S. Cl. ........................ 424/486; 424/484; 424/400; 514/772.2
(58) Field of Search ...................... 514/772.2; 424/486, 424/484

(56) References Cited

U.S. PATENT DOCUMENTS

| | | | |
|---|---|---|---|
| 4,883,785 A | 11/1989 | Chow et al. | |
| 4,900,775 A | 2/1990 | Smith et al. | |
| 5,141,961 A | * | 8/1992 | Coapman .................... 514/629 |
| 5,457,123 A | 10/1995 | Feigenbaum | |
| 6,008,192 A | * | 12/1999 | Al-Razzak et al. ........... 514/11 |

FOREIGN PATENT DOCUMENTS

| WO | WO 90/10021 | 9/1990 |
|---|---|---|
| WO | WO 95/32737 | 12/1995 |

OTHER PUBLICATIONS

Jachowicz, R., "Dissolution rates of partially water–soluble drugs from solid dispersion systems. I. Prednisolone, II. Phenytoin," International Journal of Pharmaceutics, vol. 35, pp. 1–12, (1987).

Boscolo, M. et al., "Evaluation on the suitability of differential scanning calorimetry in the performulation stability screening," Acta Technologiae et Legis Medicamenti, vol. 1, No. 1, (1990).

Chem. Ab. vol. 120:280414, 1990.*
Chem. Ab. vol. 106:162497, 1987.*

* cited by examiner

*Primary Examiner*—Thurman K. Page
*Assistant Examiner*—Liliana Di Nola-Baron
(74) *Attorney, Agent, or Firm*—Samuels, Gauthier & Stevens

(57) ABSTRACT

A process for solubilizing in water and in aqueous vehicles sparingly water-soluble pharmaceutically active substances, comprising the following operations: 1) forming a complex of the pharmaceutically active substance with a pharmaceutically acceptable non-ionic polymer capable of forming complexes with the substance, and isolating the complex in solid form; 2) dissolving again the thus obtained complex in an aqueous medium by means of a pharmaceutically acceptable surfactant. The method allows to markedly increase the water-solubility of pharmaceutically active organic compounds which are intrinsically poorly or negligibly soluble in water, in order to obtain preparations that are stable in aqueous solution and contain therapeutically and commercially useful concentrations of active ingredient.

10 Claims, 1 Drawing Sheet a TOLRESTAT
b PVP
c TOLRESTAT-PVP COMPLEX

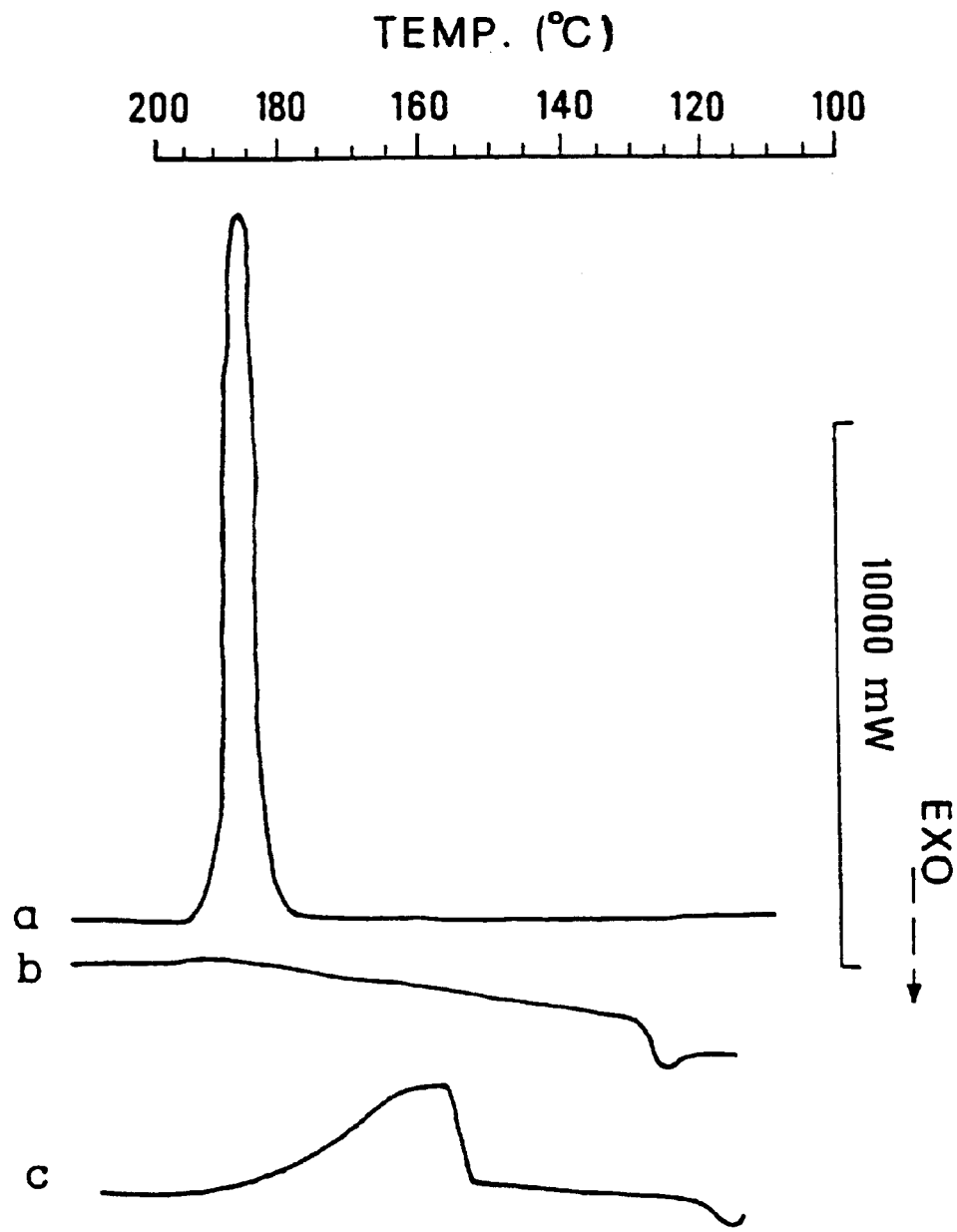

PROCESS FOR SOLUBILIZING PHARMACEUTICALLY ACTIVE INGREDIENTS IN WATER AND IN AQUEOUS VEHICLES

The present invention concerns a process for solubilizing pharmaceutically active ingredients in water and in aqueous vehicles. More specifically, this invention relates to a working procedure by means of which it is possible to remarkably increase the water-solubility of pharmaceutically active organic compounds that are intrinsically sparingly or negligibly water-soluble, so as to obtain preparations stable in aqueous solution having therapeutically and commercially useful concentrations of active ingredient.

As it is known, the poor water-solubility that characterizes many pharmaceutically active substances often results in major difficulties in the formulation, particularly in the event that easily sterilizable and administrable homogeneous aqueous solutions are desired. This particularly occurs in the fields of liquid preparations for topical ophthalmic, rhinologic, otologic, gynecologic, dermatologic use and for use on the oral mucous membranes, but it may also occur in the field of compositions for systemic administration, in particular parenteral administration (i.e. injectable solutions).

Considering specifically the ophthalmic field, it is known that there are many active ingredients sparingly soluble in water which would be extremely advantageous and effective if they could be topically administered in the form of eye-drops, or the effectiveness or ease of application of which would be increased if the concentration of the existing preparations could be increased. By way of example, there may be cited antiglaucoma agents (forskolin, dapiprazole), anti-cataract agents (tolrestat), non-steroidal anti-inflammatory drugs (piroxicam), steroidal anti-inflammatory drugs (formocortal), glucoside vasoprotective agents (rutin), fluoro-quinolone antibacterial drugs (rufloxacin), antibiotics (amphotericin B). In all of the preceding cases, the water-solutility of the active ingredient is so slight that the marketing of ophthalmic solutions based on the said actives is made impossible or unprofitable, or that the concentrations of the producible preparations are drastically limited. For instance, toirestat has been shown to be remarkably active in inhibiting aldose reductase, and this makes it quite interesting as an anticataract agent. It would be extremely useful if tolrestat could be employed in topical ophthalmic preparations rather than by systemic administration, since this would considerably reduce its side effects. The latter, on thecontrary, are not totally negligible when the product is administered systemically. Moreover, a topical formulation would enhance the drug distribution in the ocular tissues. However, eye-drop forms of toirestat are not presently on the market, very likely owing to the fact that said active principle is practically insoluble in water (0.75 mg/100 g of water, at 20° C.).

Over the years, various methods for increasing the solubility, and accordingly increasing the ease of formulation and the bioavailability, of sparingly water-soluble drugs have been studied and proposed. All said methods can be classed into one or another of the following groups:

A) chemical modifications:
  1) introduction of a ionic or ionizable group;
  2) introduction of a group that lowers the melting point;
B) physico-chemical solubilization techniques:
  1) micellar solubilization by means of surface-active agents;
  2) complexation and formation of solid solutions and suspensions by means of polymers.

The transformation of the active ingredient into a ionic or ionizable derivative (as per A1 above) is a very common solubilization method (see, e.g., S. Yalkowsky e W. Morozowich, in: Drug Design, Vol. 9, E. J. Ariens Ed., Academic Press, New York, 1980; G. L. Amidon et at., in: Design of Biopharmaceutical Properties Through Prodrugs and Analogues, Am. Pharm. Msoc., Washington, 1977, p. 281; N. J. Harper, J. Med. Pharm. Chem., 1, 467 (1959)). If the drug has free hydroxy groups hemisuccinates, phosphates, dimethyl amino acetates, amino acid esters may be formed; if, on this other hand, a carboxy group is available, esters may be formed (with amino acids, choline, dimethyl annmino ethyl alcohol, etc.). The basis of this method lies in the relationship between solubility and pH for weak acids and bases. Said basis is valid only to the point where the total solubility approaches the solubility of the ionic species (i.e. salts) (see S. F. Kramer and G. L. Flynin, J. Pharm. Sci., 61,1896 (1972)).

The method of lowering the melting point (see A2 above) is based on the concept that, in order to be solubilized, the molecules have to league the crystal lattice. Any modification of the molecule that lowers the melting point, and thus reduces the energy of the crystal lattice, tends to increase the solubility thereof in any solvent (see, e.g., N. J. Harper, Progr. Drug Res., 4, 221 (1962)).

More than 3000 scientific publications had as their subject-matter, in the last twenty years, the micellar solubilization of drugs by means of surface-active agents (as per B1 above) (see, e.g., A. T. Florence, "Drug Solubillization in Surfactant Systems" in: "Techniques of Solubilization of Drugs", S. H. Yalkowsky Ed., Vol. 12, Marcel Dekker,. New York, 1981, pp. 15–89; P. H. Elworthy et al., "Solubilization by SurfaceActive Agents", Chapman and Hall, London, 1968).

This technique has some limiting factors, such as, for instance: 1) the limited solubilizing ability of the micelles; 2) the possible short term and long term toxicity of surfactants, and 3) the simultaneous solubilization of other components of the formulation, such as preservatives, flavoring agents and dyes, with resulting alteration of the stability and activity. Coming back to the example of tolrestat, the only possibility that appears to have been Found at an experimental level in order to administer the drug as eye-drops is to produce a suspension (1% by weight) of tolrestat in an aqueous solution containing a non-ionic surfactant, i.e. Tween 80 (or polysorbate 80). Such composition could be stored (at 4° C.) for a limited time only, and had to be resuspended by shaking it every time before use. It is apparent that such a solution cannot be proposed for developments at the industrial and commercial level.

The formation of complexes, solid solutions and solid dispersions by means of the use of suitable polymers (as per B2 above) is another class of widely employed methods for increasing the water-solubility of pharmaceutically active substances.

With respect to the formation of solid solutions and suspensions, it is known that in several cases it is possible to increase the solubility of a substance even by means of a simple physical mixture. In such a case the active ingredient is incorporated in a suitable hydrophilic carrier, which increases the solubility and the bioavailability thereof without any particular chemical bonds originating between the drug and the polymer matrix. The difference between a solid solution and a solid dispersion can be defined in terms of the form of the active ingredient in a solid solution the active is present in the amorphous molecular form, while in a dispersion said active is present in a crystalline form, as fine as possible.

Even more widespread and studied is the case where the interaction between polymer and drug is such as to give rise to a true complex, wherein chemical bonds of a noncovalent nature are involved. As complexing polymers employed in the pharmaceutical field there may be cited, inter alia, polyethylene glycols, polypropylene glycols, cyclodextrins, carboxymethylcellulose, polyvinylpyrrolidone (PVP) (see, e.g., T. Higuchi et al., J. Am. Pharm. Ass., Sci. Ed., 43, 393, 398, 456 (1954); ibid., 44, 668 (1955); ibid., 46, 458, 587 (1957); J. L. Lach et al., Drug Standards, 24, 11 (1956); M. Nakano et al., J. Pharm. Sci., 65, 709 (1976)).

Co-precipitation is one of the most widespread methods for the preparation of complexes with increased solubility. By this method the substance and the polymer are dissolved in an organic solvent in which they are both soluble, and the solution is then evaporated at atmospheric pressure, under vacuum, by spray-drying or by lyophilization, to yield a dry product actually made of the complex of the treated drug. Such complexes can also be obtained by applying other methods, such as grinding and mixing the ingredients in a mill, or by extrusion of a paste containing the two products together with a minor amount of water, etc.

In devising a working method for solubilizing drugs by complexation it is necessary to take into account the molecular weight of the polymer, since the solubility of the active ingredient directly depends thereon. In general, low molecular weights are more suitable than medium to high molecular weights. The solutions stability is normally good for a great number of substances, with a maximum of two years for phenytoin co-precipitated with PVP having M.W.=50,000 (R. Jachowicz, Int J. Pharm., 35,7–12 (1987)).

Among the polymers that are employed for the formulation with sparingly water-soluble active ingredients, PVP shows quite marked complexing and solubilizing properties (see, e.g., S. Keipert et al., Pharmazie, 28, 1145–183 (1973); W. Scholtan, Makuomol. Chem., 11, 131–230 (1953); A. A. Kassem et al., Pharm. Ind., 41, 1220–1223 (1979); G. Jurgensen, Dissertation "Komplexbildung zwischen Pharmaka und makromotekularen Hilfsstoflfen", Zurich, 1966; S. Keipert et al., Pharmazie, 35, 35–40 (1980); T. Hosono et al., J. Pharm. Sci., 69, 824–826 (1980); J. A. Plaizier-Vercammen and R. E. De Neve, J. Pharm. Sci., 69, 1403–1408 (1980); 70, 1252–1256 (1981); 71, 552–556 (1982); J. A. Plaizier-Vercammen, J. Pharm. Sci., 72, 1042–1044 (1983)). A typical example is the PVP-iodine complex, the preparation of which dates back at least to 1955 (U.S. Pat. Nos. 2,706,701, 2,826,532 and 2,900,305, all to GAF Chemical Corporation). The whole amount of iodine present in said preparations is complexed, except very few p.p.m. of free iodine (H. U. Schenck et al., J. Pharm. Sci., 68, 1505–1509 (1979)). The limiting factors of this method for solubilizing iodine are the acid reaction conditions in the aqueous solutions (pH≅2) and the fact that the complexes are prone to decomposition at increasing pH.

One of the first examples of solubilization of pharmaceutically active molecules by complexation with PVP is disclosed by U.S. Pat. No. 3,089,818, published in 1963 (assigned to Baxter Laboratories, Inc.). Said document discloses the use of polyvinylpyrrolidones as complexing agents for polypeptide antibiotics substantially insoluble in water, and comprises the following steps: dissolving both the antibiotic and the polymer in non-aqueous organic solvents wherein both products are soluble, and then removing the solvent, thereby obtaining a dry complex. In comparison with the starting antibiotic, said complex shows an appreciably enhanced water-solubility.

Also within the frame of the methods disclosed above, the U.S. Pat. No. 4,900,775, published in 1990 (assigned to GAF Chemicals Corp.), proposes a method for solubilizing highly water-insoluble organic compounds by means of a complexation with PVP, in which method the whole operation of complex formation is carried out in an aqueous medium. Specifically, the insoluble active ingredient is suspended in an aqueous solution of PVP, and then the suspension is heated under stirring up to a temperature below 100° C. (preferably, 60–85° C.) for a period of time sufficient to the formation of a clear solution (preferably comprised between 1 and 1.5 hours). The solution can be used as such or it can be evaporated to give a powder of the complex.

Although the above method has, according to the authors, the advantage of not using organic solvents, it necessarily requires the heating of the actives for periods of time that are not negligible. In addition, the increase in solubility attainable appears to be of the same order of magnitude as that offered by the conventional processes effecting the complexation in an organic solvent.

For many of the pharmaceutical substances listed in the foregoing the solubility levels that can be achieved with one or another of the methods disclosed above are still insufficient to make their use in commercial products in aqueous solution proposable. As an example, it is enough to consider that tolrestat, when treated with a solubilization technique employing complexation with PVP, can increase its original solubility of 0.00075% (w/w) to a value of 0.05% (w/w). This figure cannot be proposed for a commercial application of the product in the form of eye-drops. Better results, albeit still insufficient for an industrial development, are obtained with the solubilization by means of surface-active agents. By optimizing the choice of the surfactant and the relevant amounts, a solubility of the order of 1.2% (w/w) can be attained.

Therefore, it is an object of the present invention to devise a method for treating pharmaceutically active substances poorly soluble in water, which method affords results, in terms of the overall increase of the amount of active that may be stably solubilized in water, superior to the results that can be presently achieved by the known techniques. In this context, "sparingly (or poorly, slightly, scarcely) soluble pharmaceutically active substances" are meant to be all those compounds having a biological activity the water-solubility of which, at room temperature, is too low to make commercially proposable, sufficiently active or advantageous any aqueous preparations containing said compounds as active ingredients.

To that aim, the knowledge acquired since long time about the interactions between surfactants and other components of a pharmaceutical composition has been initially considered. In particular, the interactions between surfactants and those polymer molecules that are normally present in the liquid formulations as rheological modifiers or suspension stabilizers have been considered. As a matter of fact, it is known that such interactions may affect the surfactants ability to solubilize the active ingredients. In particular, the interactions between surface active agents and polymers such as polyethylene glycol had already been studied (M. N. Jones, J. Colloid Interlace Sci., 23, 36 (1967)), as well as those between surfactants and polypropylene glycol (M. J Schwuger, J. Colloid Interface Sci., 43 491 (1973)), polyvinylpyrrolidone (M. L. Fishman, Ph.D. Thesis, Polytechnic Inst. of Brooklyn), polyvinyl alcohol (M. N. Breuer and I. D. Robb, Chem. Ind., 530 (1972)). It had been found that such interactions increase with the hydrophobic character of the macromolecule (H. Arai and S. Hovin, J. Colloid Interface Sci., 30, 372 (1969); T. isemura e A. Imanishi, J. Polymer Sdi., 33, 337 (1958)). Such studies, however, exclusively consider situations where the surfactant and the organic polymer are present at the same time in solution in the aqueous medium where the active ingredient is also possibly present, and do not offer any suggestion for the development of working solubilization methods different from the already known ones It has now been found that it is possible to drastically increase the water-solubility of pharmaceutical compounds that are scarcely soluble in water by applying a procedure consisting of two subsequent steps, in the first one of which the pharmaceutical compound is co-precipitated with a noiri-ionic complexing polymer and the resulting complex is then dried, and in the second one of which the complex is again solubilized by means of a non-ionic surface active agent By applying said procedure, which essentially consists in a combination of the two methods disclosed above under B1 and B2, it is possible to solubilize pharmaceutical actives in amounts well above the amounts afforded by the individual use of each one of said methods, and also well above, often more than twice, the sum of the said amounts.

Accordingly, the present invention specifically provides a process for solubilizing in water and in aqueous vehicles sparingly water-soluble pharmaceutically active substances, comprising, in sequence, the following operations:

1) forming a complex of such pharmaceutically active substance with a pharmaceutically acceptable non-ionic polymer capable of forming complexes with said pharmaceutically active substance, and isolating the complex in solid form;

2) dissolving again the thus obtained complex in an aqueous medium by means of a pharmaceutically acceptable non-ionic surfactant Preferably, the operation 1) is carried out by dissolving in one or more organic solvents, separately or together, said pharmaceutically active substance and said non-ionic polymer, then pooling the two solutions together in the event that the dissolution has been carried out separately, and co-precipitating the resulting complex by evaporation of the said one or more solvents. Specifically, the relative amounts of the above ingredients are preferably such that the composition of the resulting overall solution is as follows:

from 0.05% to 10% of pharmaceutically active substance;

from 1% to 50% of non-ionic polymer, and from 5% to 50% of one organic solvent or of a mixture of organic solvents, all of the above percentage amounts being by weight.

Thereafter, the solvent or the mixture of solvents are evaporated by applying one of the known methods mentioned above in connection with the formation of complexes of pharmaceutical actives, thereby bringing this complexed product in the dry form.

The section of the process according to the invention referred to as 2) is preferably carried out by adding water or an aqueous vehicle and from 1% to 50% of a non-ionic surfactant to said complex in solid form, thereby obtaining a stable and surprisingly concentrated solution of the active ingredient.

The non-ionic polymers that can be employed as complexing agents in the first section of the proposed process are suitably chosen among polyvinylpyrrolidone (PVP), cyclodextrins, polyethylene glycol (PEG), polypropylene glycol (PPG), cellulose ethers (such as methylcellulose, ethylcellulose, hydroxypropylcellulose, hydroxypropylmethylcellulose, etc.) and dextran. Particularly preferred is PVP, and specifically a soluble PVP having average molecular weight comprised in the range from 2,000 to 1,500,000, with preference for the lower molecular weights, comprised between 2,000 e 55,000.

As it is known, polyvinylpyrrolidone is a polyvinyl polymer of N-vinyl-2-pyrrolidone, obtained by radical polymerization of vinylpyrrolidone in water or in isopropyl alcohol (R. Vieweg et al., Kunststoff-Handbuch XI, Carl-Hanser-Verlag. Munich, 1971, pp. 558–569; Ullmann's Encyclopedia of lndutrial Chemistry, 5th ed., Vol. 21, VCH, 1992, pp. 752–754). In the linear chain form (which is also referred to as "povidone") PVP is readily water-soluble, and it is also soluble in many organic solvents. The cross-linked polymer form (also referred to as "crospovidone") is insoluble in virtually all common solvents.

PVP is described in the corresponding monographs "Polyvidonum" and "Povidone" of the latest editions of the European Pharmacopoeia, of the Italian Pharmacopoeia, of USP 23 etc. In these Pharmacopoeias the molecular weight of soluble PVP is expressed in terms of the value of a K parameter (H. Fikentscher, Cellulosechemie, 13, 58–64 e 71–74 (1932)), which is calculated from the relative viscosity in water and forms part of the commercial name. For instance, both in the Plasdone® line by GAF Chemicals Company and in the Kollidon® line by B.A.S.F. several grades of PVP are available, with various K-values (such as 12, 17, 25, 30 and 90 for Kollidon®). Such values correspond to various ranges of average molecular weight (in practice, from a M.W. of about 2000–3000 for Kollidon® 12 PF to a M.W. of 1,000,000–1,500,000 for Kollidon® 90 F).

It is important to consider that polymers such as PVP are not made of molecules all having the same molecular weight, rather they are mixtures comprising various proportions of molecules with different molecular weights. In the ideal case, such molecular weights have a gaussian distribution. These mixtures may be evidenced and characterized with the help of the gelpermeation chromatography. In general, said mixtures may contain up to a maximum of 15–20% of lower molecular weight fractions and about 20% of fractions of higher molecular weight Also ultrafiltration, with perfectly sized membranes, may serve to ascertain said proportion, as well as electrophoresis (M. de Vos et al., Proceedings of the 2nd Int. Symp. on Povidone, University of Ky., Lexington, 1987, pp. 10–23).

The aqueous solutions of PVP may be sterilized in autoclave (20 min. at 120° C.) with no modifications of their molecular weight as a result of this treatment. Another remarkable property of soluble PVPs is their ability of strongly reducing the irritative effects of many active ingredients. Said uritative effects may be quite considerable, for instance, in the field of ophthalmic drugs.

The molar ratios between active ingredient and complexing polytmer can be chosen, preferably, in a quite wide range: from about 1:0.1 to about 1:100, depending upon the molecular weight of the drug, on its structure, on the type and the average molecular weight of the non-ionic polymer employed. In the specific case of PVP and in the frame of the working examples presented further on, the molar ratios vary from 1:0.25 to 1:7.5, but it is; evident that different values are possible with compounds different from those shown in the examples.

As concerns the organic solvents suitable for the dissolution and co-precipitation operation recited under 1), such solvents are preferably chosen from the group consisting of monohydric alcohols with 1–4 carbon atoms, ketones (such as acetone), chlorinated solvents (such as chloroform and methylene chloride).

The formation of the PVP-drug complex is confirmed by the existing literature (K. H. Frömming et al., J. Pharm. Sci., 70, 738–743 (1981); J. A. Plaizier-Vercammen and R. E. De Neve, cited above.; S. A. Botha e A. P. Lötter, Drug Dev. Ind. Pharm., 15, 1843–1853, (1989), 16, 673–683, (1990)). The latter two authors have used, for detecting the PVP-drug complex, the method of differential scanning calorimetry (DSC). This method was also applied in the experimentation connected with the present invention.

FIG. 1 graphically compares the solubility results of the prior art processes (a, b) with the results of the present invention (c).

Specifically, as is shown by way of example in the enclosed figure with reference to the case of the PVP-tolrestat complex, the complexes obtained from the operation 1) of the process according to the invention were subjected to differential scanning calorimetry analysis, and their behaviour was compared with that of tolrestat and of PVP alone. For the analysis, exactly weighed samples of the materials were heated at a rate of 5 kcal/min in a temperature range from 100 to 250° C. As it may be ascertained from the thermograms so obtained, shown in the figure, the formation of the complex is confirmed by the fact that in the corresponding thermogram (curve c) the endothermal fusion peak of toirestat (curve a) has disappeared.

The non-ionic surface-active agents suitable for carrying out the process of the present invention comprise in general all non-ionic surfactants known for use in the pharmaceutical field, and, specifically; fatty acid esters of saccharose, fatty alcohol ethers of oligoglucosides (such as, e.g., the akylpolyglucosides known with the name "Triton"), fatty acid esters of glycerol (such as, e.g., glycerol mono/distearate or glycerol monolaurate), fatly acid esters of sorbitan (such as the "Span"s), as well as ethoxylated non-ionic surfactants, containing polyoxyethylene chains in their molecule (these being referred to by many other names, common and registered, such as polyethylene glycol, polyethylene oxide, POE, PEG, PEO, Macrogol, Carbowax, Polyox o Polyoxyl). The latter comprise, specifically, polyethoxylated fatty acid esters of sorbitan (namely, the polysorbates, such as e.g. the "Teeen"s), fatty acid esters of poly(ethylene oxide) (such as, e.g., polyoxyethylene stearates), fatty alcohol ethers of poly(ethylene oxide) (e.g., polyoxyethylated lauryl ether), alkylphenol ethers of poty (ethylene oxide) (e.g., polyethoxylated octylphenol), polyoxyethylene-polyoxypropylene block copolymers (also known as poloxamers, such as "Pluronic"), and ethoxylated fats and oils (such as, e.g., ethoxylated castor oil, or polyoxyethylated castor oil, also known as polyethylene glycol-glyceryl triricinoleate)

According to a preferred embodiment of the invention, the surfactant employed for the solubilization of the drug-polymer complex is polyethylene glycol-glyceryl triricinoleate (PEG-GTR).

PEG-GTR is obtained by reaction of glyceryl triricinoleate with ethylne oxide. In particular, the grade having the most suitable molecular weight or the purpose of the invention is produced with 35 moles of ethylene oxide per mole of glyceryl triricinoleate. The compound is described in the monograph "Macrogol 1500 glyceroltriricinoleat" of DAC 1986, 3rd Suppl., and in the monograph "Polyoxyl 35 castor oil" of the National Formulary 18. Acxording to NF 18, polyoxyl 35 castor oil is a triricinoleate ester of ethoxylated glycerol, with minor amounts of polyethylene glycol ricinoleate and of the corresponding free glycol.

The product is a light yellow, very viscous liquid (772 mPa·s at 25° C.), having relative density of 1.06, very soluble in water; its aqueous Solutions have pH 7. It is marketed under the registered trademark Cremophor EL® (B.A.S.F.), and is used as an emulsifying and solubilizing agent. It is also employed to solubilize active ingredients for injectable solutions (see, e.g., the U.S. Pat. No. 4,075,333, concerning the solubilization of vitamin compositions in non-aqueous media, for the production of injectable preparations).

As pointed out in the foregoing, the process according to the invention is particularly effective in increasing the solubility of drugs that are difficultly soluble in aqueous media, or the water-solubility of which is very low or practically null. By way of examples of cases where the method proposed was shown to be particularly advantageous there may be cited the pharmaceutically active substances mentioned in the introduction, namely forskolin, dapiprazole, tolrestat, piroxicam, formocortat, rutin, rufloxacin and anmphotericin B.

Some experimental results showing the superior effectiveness of the solubilization method according to the invention are reported in the following summary table. In this table, the solubility of each drug in water is compared with the solubility obtainable with the complexation method (with PVP) and with the solubility obtainable with the micellar solubilization method with surfactants (with PEG-GTR). In all cases it is evident that the combined method according to the invention affords solubility increases that are largely greater than the sum of the increases obtainable with each one of the prior art methods.

TABLE

Amounts of drugs solubilized at 20° C. in water, with PVP, with PEG-GTR and with the method of the invention

| Drug | Solubilizing agent | Amount (% w/w in water) | Amt. of drug solubilized at 20° C. (% w/w) |
| --- | --- | --- | --- |
| Tolrestat | none | | 0.00075 |
| | PVP (M.W. = 10,000) | 18.0 | 0.05 |
| | PEG-GTR | 6.0 | 0.60 |
| | PVP + PEG-GTR | (18.0 + 6.0) | 1.50 |
| | PVP (M.W. 10,000) | 18.0 | 0.05 |
| | PEG-GTR | 8.0 | 0.80 |
| | PVP + PEG-GTR | (18.0 + 8.0) | 2.0 |
| | PVP (M.W. = 10,000) | 18.0 | 0.05 |
| | PEG-GTR | 10.0 | 1.20 |
| | PVP + PEG-GTR | (18.0 + 10.0) | 3.0 |
| Piroxicam | none | | 0.0017 |
| | PVP (M.W. = 10,000) | 20.0 | 0.081 |
| | PEG-GTR | 2.5 | 0.13 |
| | PVP + PEG-GTR | (20.0 + 2.5) | 0.50 |
| Forskolin | none | | 0.0029 |
| | PVP (M.W. = 10,000) | 30.0 | 0.03 |
| | PEG-GTR | 10.0 | 0.05 |
| | PVP + PEG-GTR | (30.0 + 10.0) | 0.20 |
| Rutin | none | | 0.0125 |
| | PVP (M.W. = 2000–3000) | 30.0 | 0.37 |
| | PEG-GTR | 10.0 | 0.074 |
| | PVP + PEG-GTR | (30.0 + 10.0) | 1.0 |
| Formocortal | none | | 0.008 |
| | PVP (M.W. = 10,000) | 18.0 | 0.0022 |
| | PEG-GTR | 5.0 | 0.0252 |
| | PVP + PEG-GTR | (18.0 + 5.0) | 0.10 |
| Rufloxacin | none | | 0.029 |
| | PVP (M.W. = 44,000–54,000) | 15.0 | 0.24 |
| | PEG-GTR | 1.0 | 0.03 |
| | PVP + PEG-GTR | (15.0 + 1.0) | 0.30 |

Other conventional formulative ingredients, suitable for the specific use of the product considered, may be added to the solution obtained according to the teachings set forth in the foregoing. For instance, in the case of ophthalmic solutions one or more tonicity adjusting agents may be added, and to this aim the products known in the pharmaceutical art may be employed, such as, e.g., sodium chloride, potassium chloride, mannitol, dextrose, boric acid, propylene glycol. In addition, acids or bases may be added as pH adjusting agents, as well as buffers, such as Sorensen phosphate buffer or the sodium acetate—acetic acid system. The composition may also comprise preservatives and antimicrobial agents, such as benzalkonium chloride, sodium merthiolate, p-oxybenzoic acid esters, chlorbutanol, etc., and, finally, chelating agents such as the sodium salts of ethylenediamine tetraacetic acid (EDTA).

Some examples of the production of aqueous solution compositions by means of the process according to the invention are reported below, for illustrative purposes only, with specific reference to the ophthalmic field. It is evident, however, that the persons skilled in the art will easily formulate solutions suitable for use in other fields, by adding the appropriate excipients.

EXAMPLE 1

| Tolrestat | g 3.0 |
|---|---|
| PVP (M.W. = 10,000) | g 18.0 |
| Cremophor EL ® | g 10.0 |
| benzalkonium chloride | g 0.01 |
| Sörensen phosphate buffer pH 7,4 | q.s. to 100.00 g |

The solution is prepared by the following procedure:

3 g (8.4 mmoles) of tolrestat are dissolved in 50 ml of acetone. Separately, 18 g (1.8 mmoles) of PVP (M.W.=10,000) are dissolved in 50 ml of acetone. The two solutions, pooled together, are evaporated to dryness in a rotary evaporator at room temperature, and the complex thus formed is kept overnight under vacuum, in order to completely eliminate the residual solvents.

The complex is then mixed with 10.0 g of PEG-GTR and, while stirring the phosphate buffer containing benzalkonium chloride previously disolved therein is added.

The solution thus obtained is filtered and packaged.

EXAMPLE 2

Formulation: as in Example 1.

Preparation: 3 g (8.4 mmoles) of toirestat are dissolved in 50 ml of acetone. 18 g (1.8 mmoles) of PVP (M.W.=10,000) are added to the solution. After having obtained a dear solution, the mixture is dried in a notary evaporator at room temperature. The complex thus formed is treated as iin the previous example, and 10.0 g of PEG-GTR are then added, completing the preparation as described in said example.

EXAMPLE 3

Formulation: as in Example 1.

Preparation: 3 g (8.4 mmoles) of toirestat and 18.0 g (1.8 mmoles) of PVP (M.W.=10,000) are dissolved according to the method of Example 1 or the method of Example 2, and the solution is then evaporated by spray-drying.

The complex obtained is then mixed with 10.0 g of PEG-GTR, completing the preparation as described in Example 1.

EXAMPLE 4

Formulation: as in Example 1.
Preparation: the same procedure as in Example 1 (first variant), or the same procedure as in Example 2 (second variant), is followed, replacing acetone with methyl alcohol.

EXAMPLE 5

Formulation: as in Example 1.
Preparation: the same procedure as in Example 1 (first variant), or the same procedure as in Example 2 (second variant), is followed, replacing acetone with chloroform.

EXAMPLE 6

Formulation: as in Example 1.
Preparation: the same procedure as in Example 1 (first variant), or the same procedure as in Example 2 (second variant), is followed, replacing acetone with a mixture of chloroform and methyl alcohol.

EXAMPLE 7

| Tolrestat | g 1.5 |
|---|---|
| PVP (M.W. = 10,000) | g 18.0 |
| Cremophor EL ® | g 6.0 |
| benzalkonium chloride | g 0.01 |
| Sörensen phosphate buffer pH 7,4 | q.s. to 100.00 g |

The solution is prepared by the same procedure as in Example 1, except that the amounts employed are those listed above.

EXAMPLE 8

Formulation: as in Example 7, except for the buffer.
Preparation: the same procedure as in Example 1 is followed, replacing the Sorensen phosphate buffer with distilled water.

EXAMPLE 9

| Tolrestat | g 3.0 |
|---|---|
| PVP (M.W. = 10,000) | g 18.0 |
| saccharose monolaurate | g 12.0 |
| methyl p-oxybenzoate | g 0.1 |
| Sörensen phosphate buffer pH 7,4 | q.s. to 100.00 g |

The solution is prepared by the same procedure as in Example 1, replacing the non-ionic surfactant Cremophor EL® with saceharose moncdaurate and the preservative benzalkonium chloride with methyl p-oxybenzoate.

EXAMPLE 10

| Piroxicam | g 0.50 |
|---|---|
| PVP (M.W. = 10,000) | g 20.0 |
| Cremophor EL ® | g 2.5 |
| benzalkonium chloride | g 0.01 |
| isotonic phosphate buffer pH 7,4 | q.s. to 100.00 g |

The solution is prepared by the following procedure:

0.50 g (1.5 mmoles) of piroxicam and 20.0 g (2 mmoles) of PVP (M.W.=10,000) are treated following the same procedure as in the first part of Example 1. The complex thus obtained is then mixed with 2.5 g of PIG-GTR, completing the preparation as described in the second part of Example 1.

EXAMPLE 11

| Piroxicam | g 0.50 |
|---|---|
| PVP (M.W. = 10,000) | g 20.0 |
| Cremophor EL ® | g 2.5 |
| sodium merthiolate | g 0.005 |
| distilled water | q.s. to 100.00 g |

The solution is prepared by the following procedure:

0.50 9 (1.5 mmoles) of piroxicam and 20.0 g (2 mmoles of PVP (M.W.=10,000) are treated following the same procedure as in the first part of Example 1. The complex thus obtained is then mixed with 2.5 g of PEG-GTR, completing the preparation as described in the second part of Example 1, but replacing the benzalkonium chloride preservative with sodium merthiolate and the buffer solution with distilled water.

EXAMPLE 12

| Forskolin | g 0.20 |
|---|---|
| PVP (M.W. = 10,000) | g 30.0 |
| Cremophor EL ® | g 10.0 |
| benzalkonium chloride | g 0.01 |
| distilled water | q.s. to 100.00 g |

The solution is prepared by the following procedure:

0.20 g (0.48 mmoles) of forskolin and 30.0 g (3 mmoles) of PVP (M.W.=10,000) are treated following the same procedure as in the first part of Example 1. The complex thus obtained is then mixed with 10.0 g of PEG-GTR, completing the preparation as described in the second part of Example

EXAMPLE 13

| Rutin | g 1.0 |
|---|---|
| PVP (M.W. = 2000–3000) | g 30.0 |
| Cremophor EL ® | g 10.0 |
| benzalkonium chloride | g 0.01 |
| distilled water | qs. to 100.00 g |

The solution is prepared by the following procedure:

1.0 g (1.63 mmoles) of rutin and 30.0 g (12 mmoles) of (M:W.=2000–3000) are treated following the same procedure as in the first part of Example 1. The complex thus obtained is then mixed with 10.0 g of PEG-GTR, completing the preparation as described in the second part of Example 1.

The present invention has been disclosed with particular reference to some specific embodiments thereof, but it should be understood that modifications and changes may be made by the persons skilled in the art without departing from the scope of the invention as defined in the appended claims.

What is claimed is:

1. A process for solubilizing in water and in aqueous vehicles sparingly water-soluble pharmaceutically active substances, comprising, in sequence, the following operations:

1) forming a complex of such pharmaceutically active substance with a pharmaceutically acceptable non-ionic polymer capable of forming complexes with said pharmaceutically active substance, and isolating the complex in solid form;

2) dissolving again the thus obtained complex in an aqueous medium by means of a pharmaceutically acceptable non-ionic surfactant.

2. A process according to claim 1, wherein said operation 1) is carried out by dissolving in one or more organic solvents, separately or together, said pharmaceutically active substance and said non-ionic polymer, then pooling the two solutions together in the event that the dissolution has been carried out separately, and co-precipitating the resulting complex by evaporation of said one or more solvents.

3. A process according to claim 2, wherein said operation 1) comprises the following steps:

1a) combining and mixing up to dissolution, separately or together, said pharmaceutically active substance and said non-ionic polymer with said one or more organic solvents, in such a way that the composition of the resulting overall solution is as follows:
   from 0.05% to 10% of pharmaceutically active substance;
   from 1% to 50% of non-ionic polymer; and
   from 5% to 50% of one organic solvent or of a mixture of organic solvents,
   all of the above percentage amounts being by weight; and 1b) evaporating said one or more solvents to give said complex in solid form.

4. A process according to claim 2, wherein said operation 2) comprises the following step:

2a) adding water or an aqueous vehicle and from 1% to 50% of a non-ionic surfactant to said complex in solid form.

5. A process according to claim 1, wherein said pharmaceutically acceptable non-ionic polymer capable of forming complexes is chosen from the group consistig of: polyvinylpyrrolidone, cyclodextrins, polyethylene glycol, polypropylene glycol, cellulose ethers and dextran.

6. A process according to claim 5, wherein said non-ionic polymer is soluble PVP, having an average molecular weight comprised in the range from 2,000 to 1,500,000.

7. A process according to claim 1, wherein said non-ionic surfactant is chosen from the group consisting of: fatty acid esters of saccharose, fatty alcohol ethers of oligoglucosides, fatty acid esters of glycerol, fatty acid esters of sorbitan, polyethoxylated fatty acid esters of sorbitan, fatty acid esters of poly(ethylene oxide), fatty alcohol ethers of poly (ethylene oxide), alkylphenol ethers of poly(ethylene oxide), polyoxyethylene-polyoxypropylene block copolymers, and ethoxylated fats and oils.

8. A process according to claim 7, wherein said surfactant is polyethylene glycol-lyceryl triricinoleate.

9. A process according to claim 2, wherein said one or more organic solvents are chosen from the group consisting of: monohydric alcohols with 1–4 carbon atoms, ketones, and chlorinated solvents.

10. A process according to claim 1, wherein said pharmaceuticauly active substance is chosen from the group consisting of: forskolin, dapiprazole, tolrestat, piroxicam, formocortal, rutin, rufloxacin, and amphotericin B.

* * * * *